(12) United States Patent
Kawahara (10) Patent No.: US 7,936,452 B2
(45) Date of Patent: May 3, 2011

(54) INSPECTION APPARATUS, EXPOSURE APPARATUS, AND METHOD OF MANUFACTURING DEVICE

(75) Inventor: Atsushi Kawahara, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 100 days.

(21) Appl. No.: 12/505,530

(22) Filed: Jul. 20, 2009

(65) Prior Publication Data

US 2010/0020316 A1    Jan. 28, 2010

(30) Foreign Application Priority Data

Jul. 25, 2008  (JP) .................................. 2008-192686

(51) Int. Cl.
*G01N 21/00* (2006.01)
(52) U.S. Cl. .................................. 356/237.4; 356/239.8
(58) Field of Classification Search .............. 356/237.3, 356/237.4, 239.7, 239.8
See application file for complete search history.

(56) References Cited

U.S. PATENT DOCUMENTS

| | | | | |
|---|---|---|---|---|
| 4,831,274 A | * | 5/1989 | Kohno et al. ............ | 250/559.49 |
| 4,999,510 A | * | 3/1991 | Hayano et al. ............ | 250/559.41 |
| 5,274,434 A | * | 12/1993 | Morioka et al. ............ | 356/237.4 |
| 5,305,079 A | * | 4/1994 | Albrecht et al. ............ | 356/237.2 |
| 5,363,187 A | * | 11/1994 | Hagiwara et al. ............ | 356/237.3 |
| 5,581,348 A | | 12/1996 | Miura et al. | |
| 5,585,916 A | | 12/1996 | Miura et al. | |
| 5,680,207 A | * | 10/1997 | Hagiwara ............ | 356/237.3 |
| 6,532,065 B1 | * | 3/2003 | Grimme et al. ............ | 356/237.2 |
| 7,388,659 B2 | * | 6/2008 | Kobayashi ............ | 356/237.3 |
| 7,719,669 B2 | * | 5/2010 | Matsui et al. ............ | 356/237.1 |
| 7,733,471 B2 | * | 6/2010 | Mitome ............ | 356/237.1 |
| 2008/0013084 A1 | * | 1/2008 | Matsui et al. ............ | 356/237.5 |

FOREIGN PATENT DOCUMENTS

| | | |
|---|---|---|
| JP | 07-005115 A | 1/1995 |
| JP | 07-043312 A | 2/1995 |

OTHER PUBLICATIONS

U.S. Appl. No. 12/424,468, filed Apr. 15, 2009, Inventor: Kohei Maeda, "Foreign Particle Inspection Apparatus, Exposure Apparatus, and Method of Manufacturing Device".

* cited by examiner

*Primary Examiner* — Roy Punnoose
(74) *Attorney, Agent, or Firm* — Canon U.S.A., Inc., IP Division (57) ABSTRACT

An inspection apparatus includes a projecting unit, a first receiving unit, a second receiving unit, and a controller. The projection unit is configured to project linear light on a surface of an object. The first and second receiving units are configured to receive scattered light of the projected linear light. The controller is configured to scan the projecting unit, the first and second receiving units and determine the present or absence of a foreign substance on the surface based on intensity distribution signals output from the first and second receiving units.

17 Claims, 10 Drawing Sheets

INSPECTION APPARATUS, EXPOSURE APPARATUS, AND METHOD OF MANUFACTURING DEVICE

BACKGROUND OF THE INVENTION

1. Field of the Invention

The present invention relates to an inspection apparatus, an exposure apparatus, and a method of manufacturing a device.

2. Description of the Related Art

In general, in a manufacturing process for ICs and LSIs, an exposure apparatus such as a stepper or a mask aligner transfers a circuit pattern formed on a reticle, a photomask, or the like onto a wafer coated with a resist.

In this transfer step, if a pattern defect or a foreign substance such as dust exists on a reticle or the like, the foreign substance is also transferred onto the wafer at the same time, resulting in a decrease in the yield of IC and LSI manufacture. In particular, when a reticle is used and circuit patterns are repeatedly exposed on many shot areas on a wafer by the step-and-repeat method, if a harmful foreign substance exists on the reticle, the foreign substance is exposed on the entire wafer surface. This greatly decreases the yield of ICs and LSIs.

Detecting the presence of a foreign substance on a reticle is therefore indispensable to a manufacturing process for ICs and LSIs. In general, a foreign substance inspection apparatus using the property of a foreign substance that isotropically scatters light is used.

For example, the surface of an object to be inspected is inspected by projecting a parallel beam onto the surface of the object from obliquely upward, and forming an image of a foreign substance on a one-dimensional image sensor (sensory array) by making the sensor receive scattered light from the foreign substance via a graded index microlens array (see Japanese Patent Laid-Open Nos. 7-43312 and 7-5115).

Figure 10:
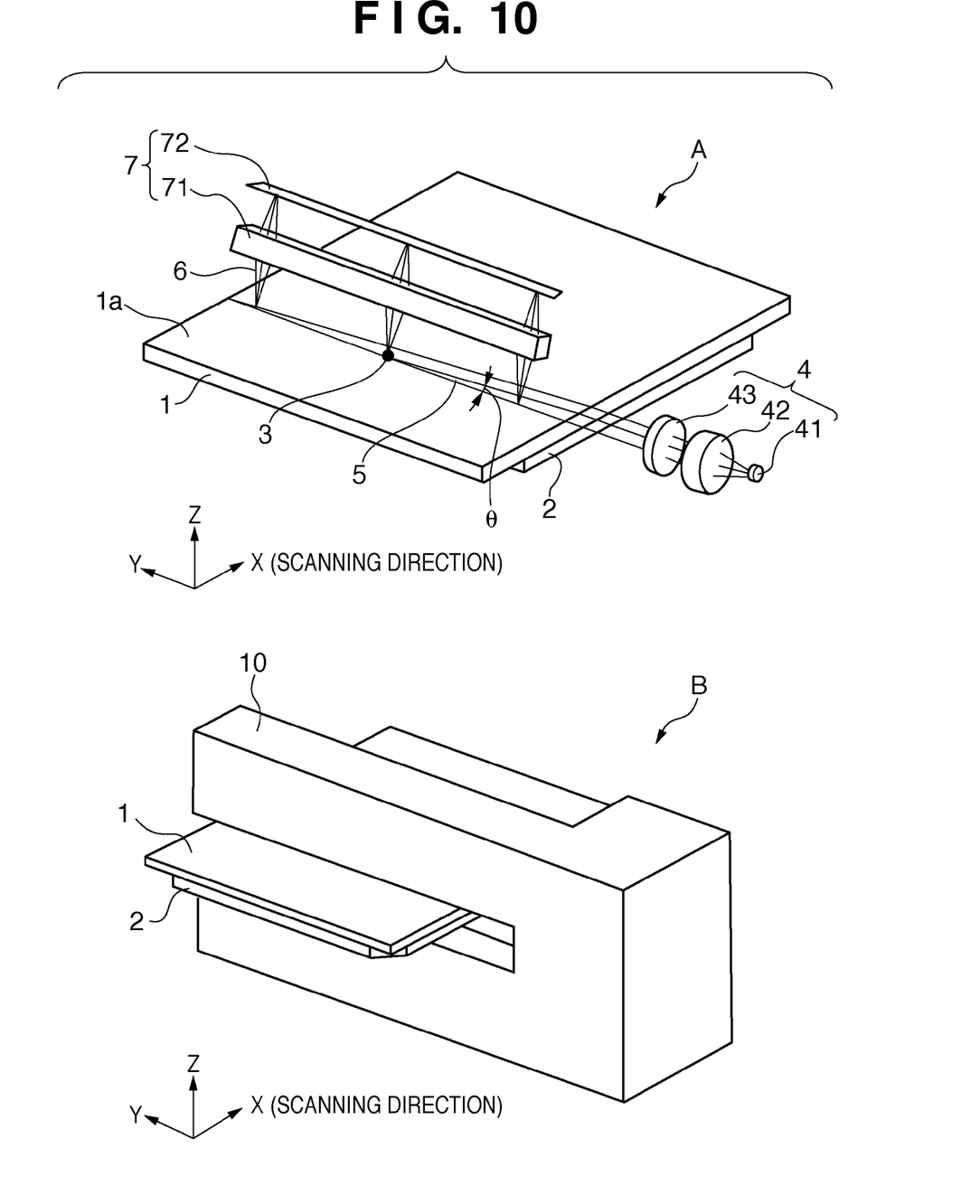
FIG. 10 is a schematic view of a conventional foreign substance inspection apparatus.

FIG. 10 shows the basic arrangement of an optical system of a foreign substance inspection apparatus disclosed in Japanese Patent Laid-Open Nos. 7-43312 and 7-5115. For simple explanation, only the optical system for inspecting a foreign substance on a blank surface of a reticle will be described below. In practice, however, this apparatus also includes an optical system for inspecting a foreign substance on a pellicle film that protects a circuit pattern surface of a reticle against foreign substances. Reference numeral 2 in FIG. 10 denotes a pellicle frame attached with a pellicle film.

A collimator lens 42 converts a laser beam which is emitted by a semiconductor laser 41 and has a divergence angle into a parallel beam. A λ/2 plate 43 then makes the polarization axis of the projected light parallel to a plane including the optical axis of the projected light and the optical axis of the light received by a light receiving unit 7. The laser beam is incident on the surface of an object to be inspected at an angle θ near parallel to the surface of the object. This forms a linear light projection area 5 by the laser beam on a blank surface 1a as a surface to be inspected.

If a foreign substance 3 exists on the light projection area 5, scattered light is generated by the foreign substance 3. An imaging lens 71 (lens array) which has lenses arrayed along the longitudinal direction of the light projection area 5 to receive scattered light focuses the scattered light on a line sensor 72. The imaging lens 71 is configured to form an image of the light projection area 5 on the line sensor 72. As denoted by reference symbol B in FIG. 10, this apparatus inspects foreign substances on the entire blank surface 1a by linearly scanning an overall optical system 10 in a direction perpendicular to the longitudinal direction of the light projection area 5 and parallel to the blank surface 1a, that is, the X direction.

There is also proposed an inspection apparatus which includes another light receiving unit 7' having the same arrangement as that of the light receiving unit 7 in FIG. 10, and compares inspection maps from the two light receiving units to remove a false foreign substance signal generated when a light beam is scattered by a circuit pattern or the like, thereby accurately detecting the position and size of a foreign substance (see Japanese Patent Application No. 2008-108291 (U.S. patent application Ser. No. 12/424,468)).

Figure 2:
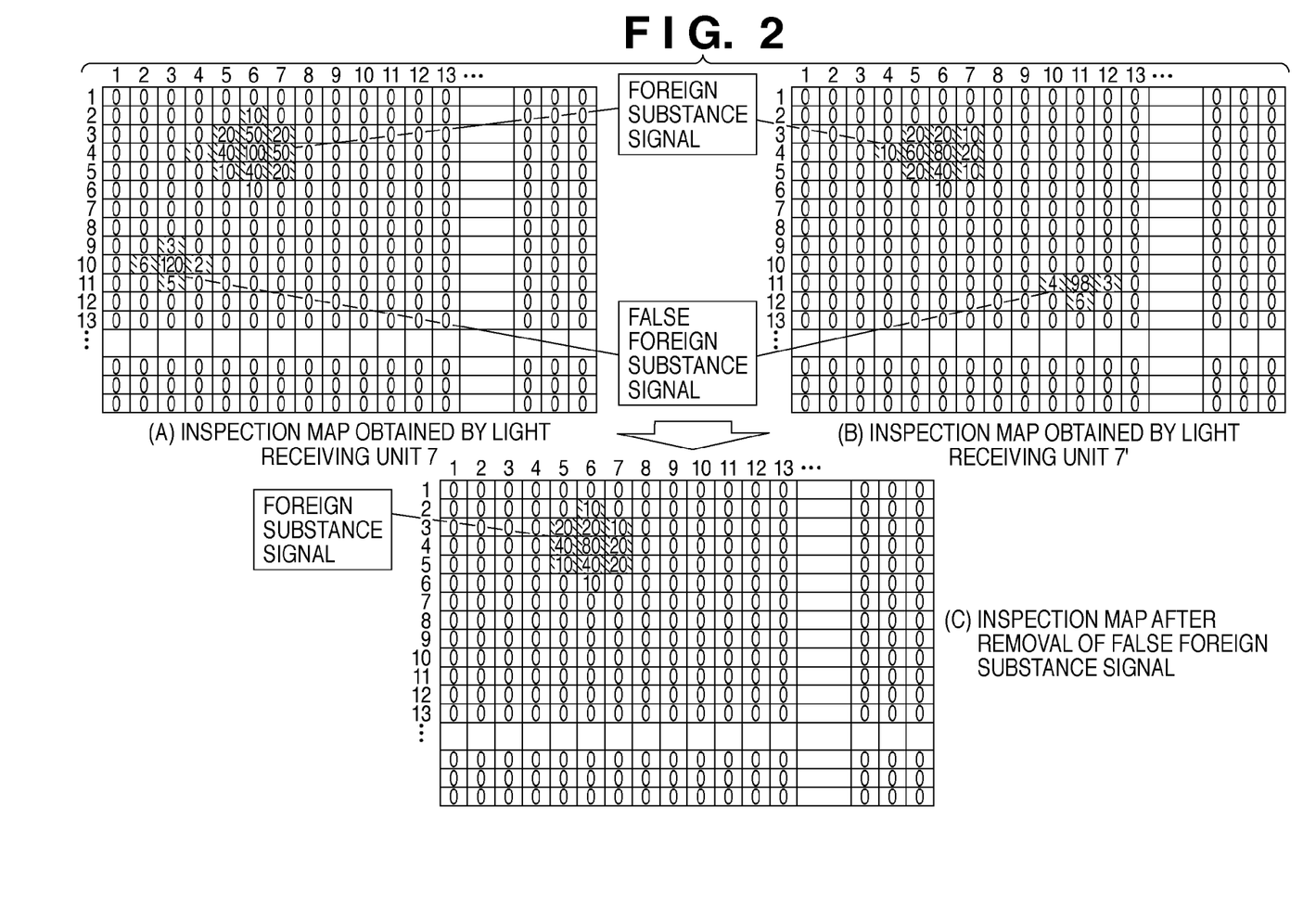
FIG. 2 is a schematic diagram showing an example of the processing of removing false foreign substance signals.

FIG. 2 shows a technique of removing a false foreign substance signal. Reference symbol A in FIG. 2 denotes an example of the inspection map obtained from the light receiving unit 7; and B, an example of the inspection map obtained from the light receiving unit 7'. Since scattered light from a foreign substance commonly appears in both the inspection maps, it is possible to extract only a foreign substance signal by removing a signal appearing in only one of the inspection maps as a false foreign substance signal. Reference symbol C denotes an inspection map after the removal of false foreign substance signals from the two inspection maps A and B.

Figure 4:
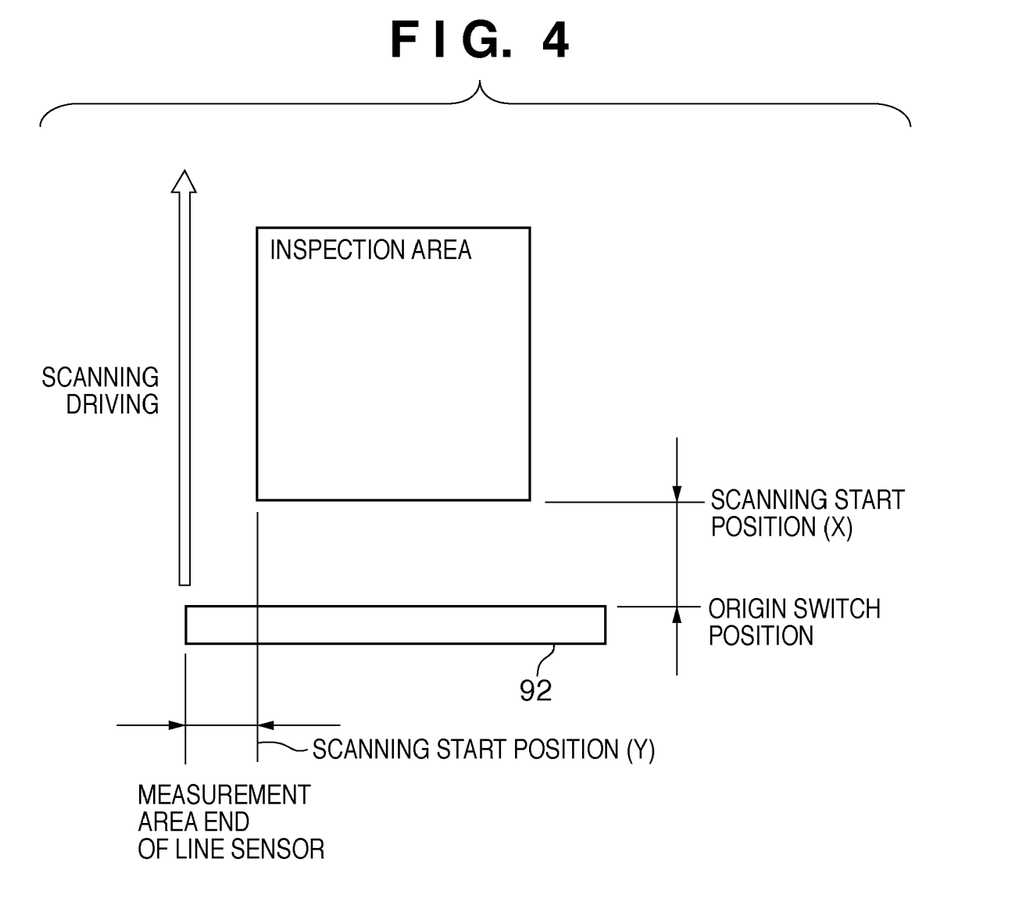
FIG. 4 is a conceptual diagram showing scanning start positions.

A basic management method for positions at which the foreign substance inspection apparatus starts inspection, that is, positions at which the light receiving unit starts scanning, will be described with reference to FIG. 4. Each scanning start position is managed by the distance from the origin switch position. The longitudinal direction of the line sensor is managed by the distance from a measurement end point of the line sensor. Since the origin switch and the line sensor have mounting errors, only a foreign substance within a predetermined range on a reticle placed in the foreign substance inspection apparatus is inspected by adjusting the scanning start position for each line sensor at the time of assembly of the foreign substance inspection apparatus.

A conventional technique of adjusting the scanning start positions of a plurality of light receiving units will be described. The conventional adjustment technique uses an adjustment ceramic plate (to be referred to as an "adjustment plate" hereinafter) on which predetermined patterns like the sign "+" are printed. This technique inspects the adjustment plate placed in the center of a stage in the foreign substance inspection apparatus, and adjusts the respective scanning start positions of a plurality of light receiving units such that the display position of a pattern image appearing in the obtained inspection map is located in the center of the inspection area. However, the conventional adjustment technique can only obtain an adjustment accuracy of about 1 mm at best.

Figure 3:
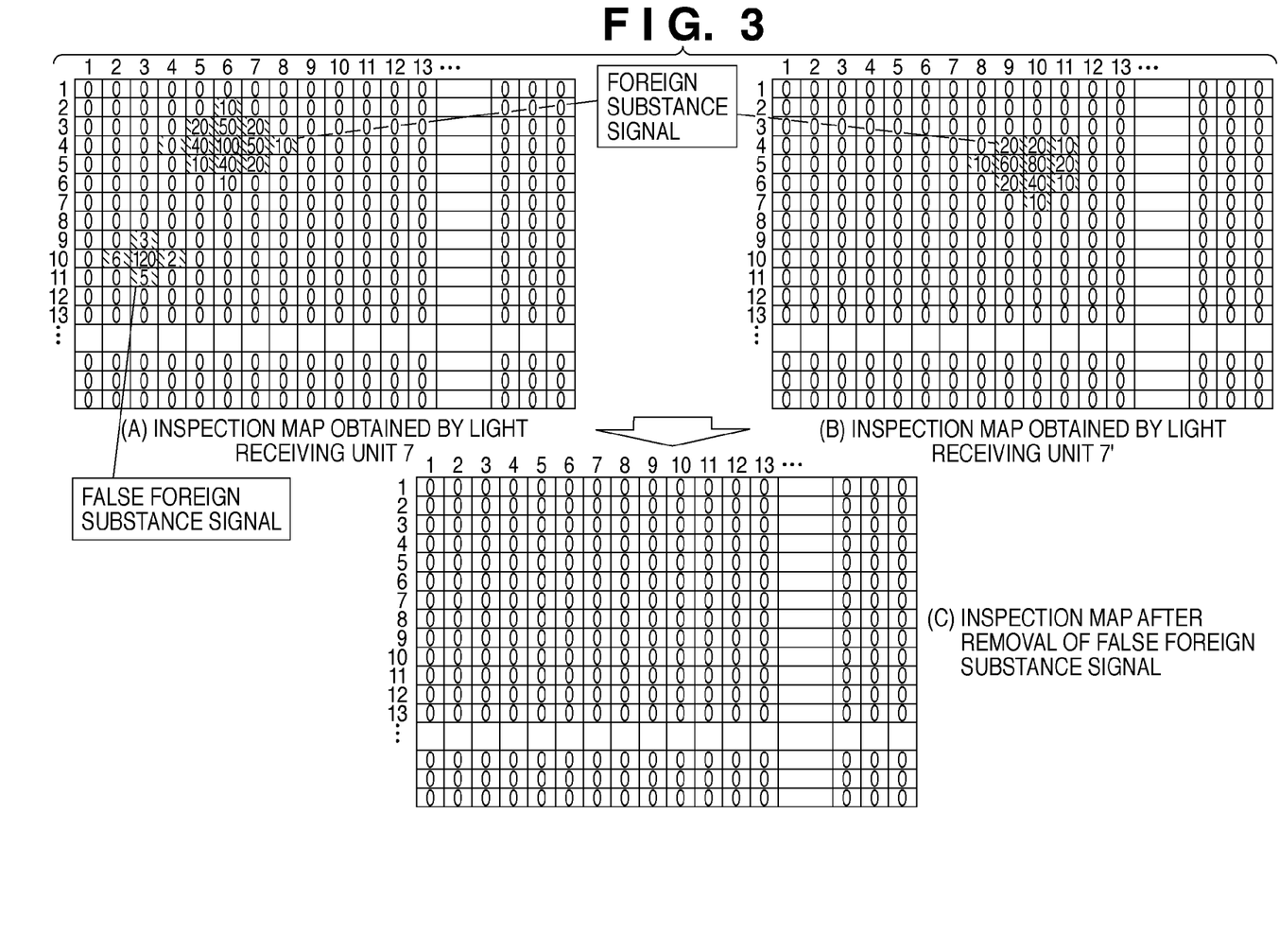
FIG. 3 is a schematic diagram showing an example of the processing of removing a false foreign substance signal.

FIG. 3 shows an example of inspection maps obtained by the conventional technique which has adjusted the scanning start positions of a plurality of light receiving units by using an adjustment plate. Reference symbol A denotes the inspection map obtained from one light receiving unit 7; B, the inspection map obtained from the other light receiving unit 7'; and C, the inspection map obtained by removing the false foreign substance signal generated based on the inspection maps A and B.

Foreign substance signals are respectively detected in the inspection maps A and B. Assume that a signal appearing only in one of the inspection maps is removed as a false foreign substance signal. In this case, if the light receiving units detect a foreign substance at different positions as in the case of the inspection maps A and B, the foreign substance signal may be deleted in the inspection map C.

As described above, according to the conventional technique of adjusting scanning start positions by using an adjustment plate, since the accuracy of adjustment of scanning start positions is insufficient, even a foreign substance signal may be deleted in the process of removing a false foreign substance signal by using a plurality of light receiving units.

SUMMARY OF THE INVENTION

The present invention allows a foreign substance inspection apparatus including a plurality of light receiving units to perform accurate inspection.

According to an aspect of the present invention, there is provided an inspection apparatus comprising a light projecting unit configured to project linear light on a surface of an object to be inspected, a first light receiving unit and a second light receiving unit configured to receive scattered light of light projected on the surface by the light projecting unit, which is generated by the surface, and a controller configured to relatively scan the light projecting unit, the first light receiving unit, and the second light receiving unit along the surface while maintaining a positional relationship between the light projecting unit, the first light receiving unit, and the second light receiving unit and determine the presence/absence of a foreign substance on the surface based on intensity distributions of signals output from the first light receiving unit and the second light receiving unit, the controller causing the inspection apparatus to perform foreign substance inspection a plurality number of times while changing a positional relationship between a tentative first start position at which the first light receiving unit starts scanning and a tentative second start position at which the second light receiving unit starts scanning, calculating an overlapping degree between an intensity distribution of a signal output from the first light receiving unit and an intensity distribution of a signal output from the second light receiving unit for each of the plurality of foreign substance inspections, and determining a scanning start position of each of the first light receiving unit and the second light receiving unit to inspect the surface of the object based on the positional relationship between the tentative first start position and the tentative second start position which exhibits a maximal overlapping degree among the plurality of calculated overlapping degrees.

According to another aspect of the present invention, there is provided an inspection apparatus comprising a projecting unit configured to project linear light on a surface of an object; a first receiving unit and a second receiving unit configured to receive scattered light of projected linear light; and a controller configured to scan the projecting unit, the first and second receiving units, along the surface while maintaining a positional relationship between the projecting unit, the first and second receiving units, and to determine the presence/absence of a foreign substance on the surface based on intensity distributions of signals output from the first and second receiving units, wherein the controller causes the inspection apparatus to perform foreign substance inspection a plurality number of times while changing a positional relationship between a first start position at which the first receiving unit starts scanning and a second start position at which the second receiving unit starts scanning, calculates an overlapping degree between an intensity distribution of a signal output from each of the first and second receiving units for each of the plurality of foreign substance inspections, and determines a scanning start position of each of the first and second receiving units to inspect the surface of the object based on the overlapping degree.

According to the present invention, for example, a foreign substance inspection apparatus including a plurality of light receiving units can perform accurate inspection.

Further features of the present invention will become apparent from the following description of exemplary embodiments with reference to the attached drawings.

DESCRIPTION OF THE EMBODIMENTS

Figure 1:
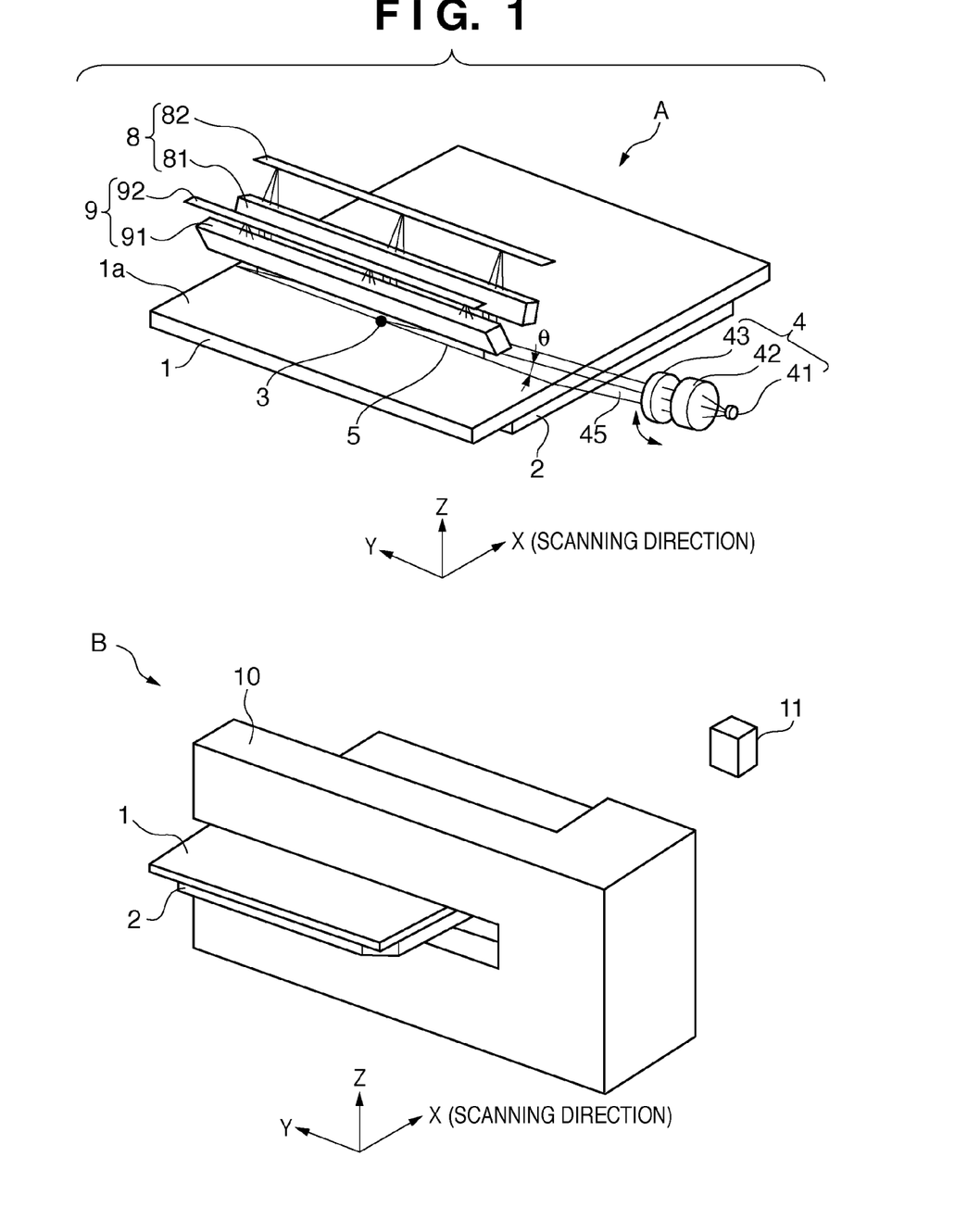
FIG. 1 is a schematic view showing a foreign substance inspection apparatus.

FIG. 1 is a view showing the basic arrangement of an optical system of a foreign substance inspection apparatus according to a first embodiment. For the sake of simplicity, only an optical system for inspecting a foreign substance on a blank surface 1a of a reticle 1 will be described below. However, this embodiment can also include an optical system for inspecting a foreign substance on a pellicle film which protects the circuit pattern surface of the reticle 1 against foreign substances. Reference numeral 2 in FIG. 1 denotes a pellicle frame attached with a pellicle film. Therefore, an object to be inspected by the foreign substance inspection apparatus can be at least one of the reticle 1 and the pellicle film.

A light projecting unit 4 which projects linear light 45 on the surface of the reticle 1 as an object to be inspected includes a semiconductor laser 41, a collimator lens 42, and a $\lambda/2$ plate 43, as in the arrangement shown in FIG. 10. It is possible to use a polarizing filter, a $\lambda/4$ plate, an optical polarizing element, or the like instead of the $\lambda/2$ plate 43. A first light receiving unit 8 which receives scattered light on the blank surface 1a which is projected by the light projecting unit 4 has the same arrangement as that of the light receiving unit 7 in FIG. 10. The foreign substance inspection apparatus in FIG. 1 also includes a second light receiving unit 9 having the same arrangement as that of the first light receiving unit 8. This apparatus also includes a controller 11 which determines the presence/absence of a foreign substance on a blank surface 1a based on the intensity distributions of the signals output from the two light receiving units 8 and 9. The controller 11 can also determine the size of a foreign substance.

As denoted by reference symbol B in FIG. 1, the foreign substance inspection apparatus inspects a foreign substance on the entire blank surface 1a by scanning an overall optical system 10 relative to the reticle 1 in a direction perpendicular to the longitudinal direction of a light projection area 5 and parallel to the blank surface 1a, that is, along the X direction. When inspecting a foreign substance, the apparatus maintains the positional relationship between the light projecting unit 4 and the two light receiving units 8 and 9.

The light projecting unit 4 is placed such that the optical axis of light projected by the light projecting unit 4 is inclined at θ with respect to the blank surface 1a.

Figure 7:
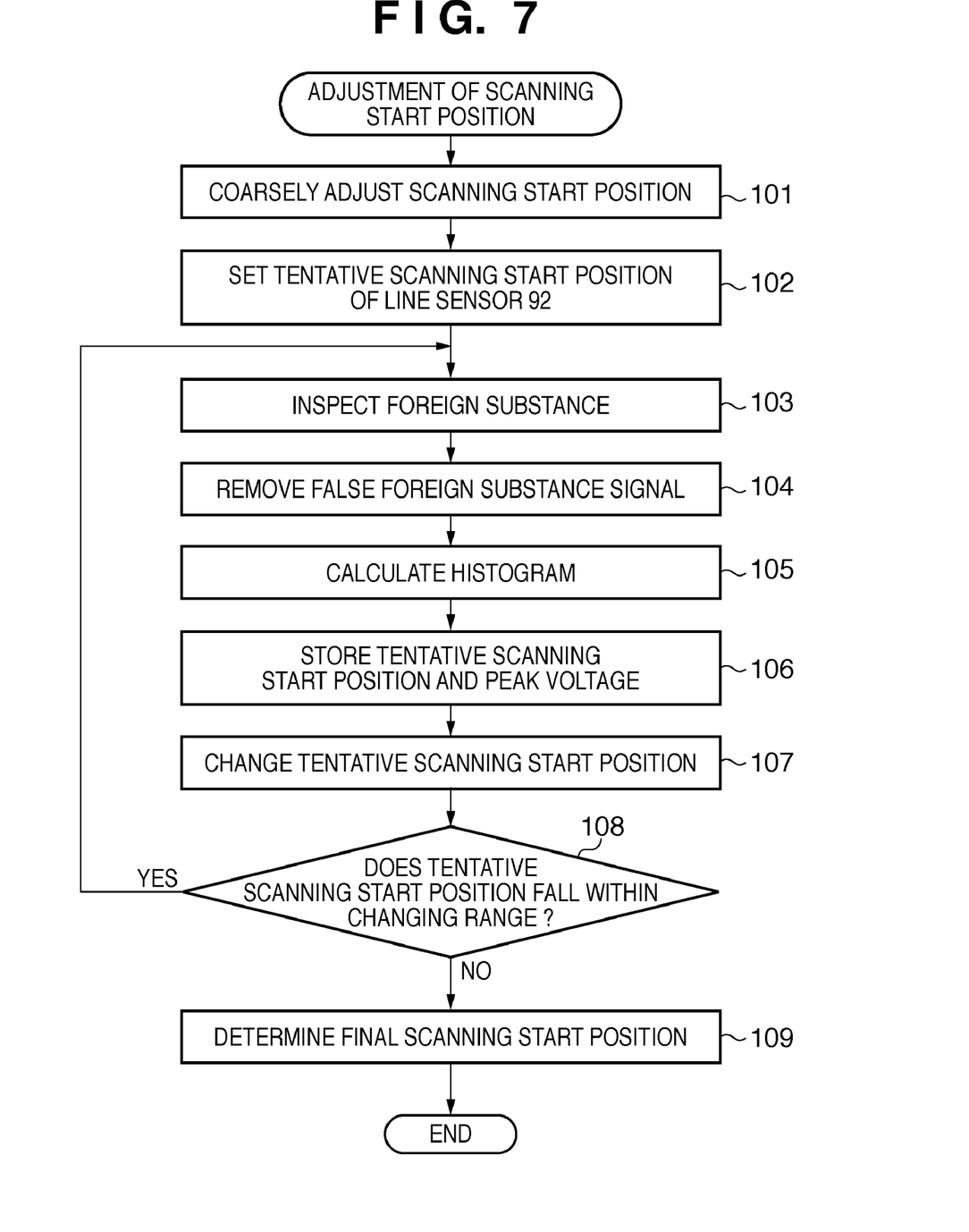
FIG. 7 is a flowchart for a technique of determining a scanning start position.

An example of a technique of adjusting the scanning start positions at which the two light receiving units, more specifically, two line sensors 82 and 92, start scanning in the X direction will be described with reference to FIG. 7. Reference numerals 81 and 91 mean imaging lens sensors (lens arrays).

In step 101, the operator coarsely adjusts (coarse adjustment) the scanning start positions of the line sensors 82 and 92. It is possible to perform this coarse adjustment by the conventional adjustment technique of placing an adjustment plate having predetermined patterns like the sign "+" at a predetermined position in a foreign substance inspection apparatus and adjusting the scanning start positions so as to place the images captured by the line sensors 82 and 92 at predetermined positions. Performing this coarse adjustment can determine the first scanning start position (X82, Y82) of the line sensor 82. The coarse adjustment also tentatively determines a tentative second scanning start position (X92, Y92) of the line sensor 92. The operator inspects a foreign substance by using the line sensor 82 whose scanning start position has been determined, and the foreign substance inspection apparatus stores the inspection map (denoted by reference symbol A in FIG. 5) of the intensity distribution of the signal output from the line sensor 82. Note that it is possible to perform foreign substance inspection using the line sensor 82 whose scanning start position has been determined and foreign substance inspection using the line sensor 92 in the following step with respect to a glass plate coated with a reference particle as a target.

In steps 102 to 108, the apparatus performs fine adjustment processing to strictly match the tentative second scanning start position of the line sensor 92 with the first scanning start position of the line sensor 82.

In step 102, the controller 11 of the foreign substance inspection apparatus tentatively sets a tentative second scanning start position (X82−0.5 mm) of the line sensor 92. This operation initially sets the positional relationship between the first scanning start position of the line sensor 82 and the tentative second scanning start position of the line sensor 92. Note that (X82−0.5 mm) indicates that the tentative second scanning start position of the line sensor 92 which the controller 11 recognizes is located ahead of the first scanning start position of the line sensor 82, determined in step 101, by 0.5 mm. The first and second scanning start positions of the line sensors 82 and 92 are expressed with reference to the origin switch position shown in FIG. 4. The tentative second scanning start position (X82−0.5 mm=10.5 mm) of the line sensor 92 in FIG. 5, which is tentatively set first, indicates that the position is spaced apart from the origin switch position by 10.5 mm.

In step 103, the line sensor 92 starts inspecting a foreign substance from the tentative second scanning start position (X82−0.5 mm=10.5 mm). The controller 11 calculates a corresponding inspection map (denoted by reference symbol B in FIG. 5).

Figure 5:
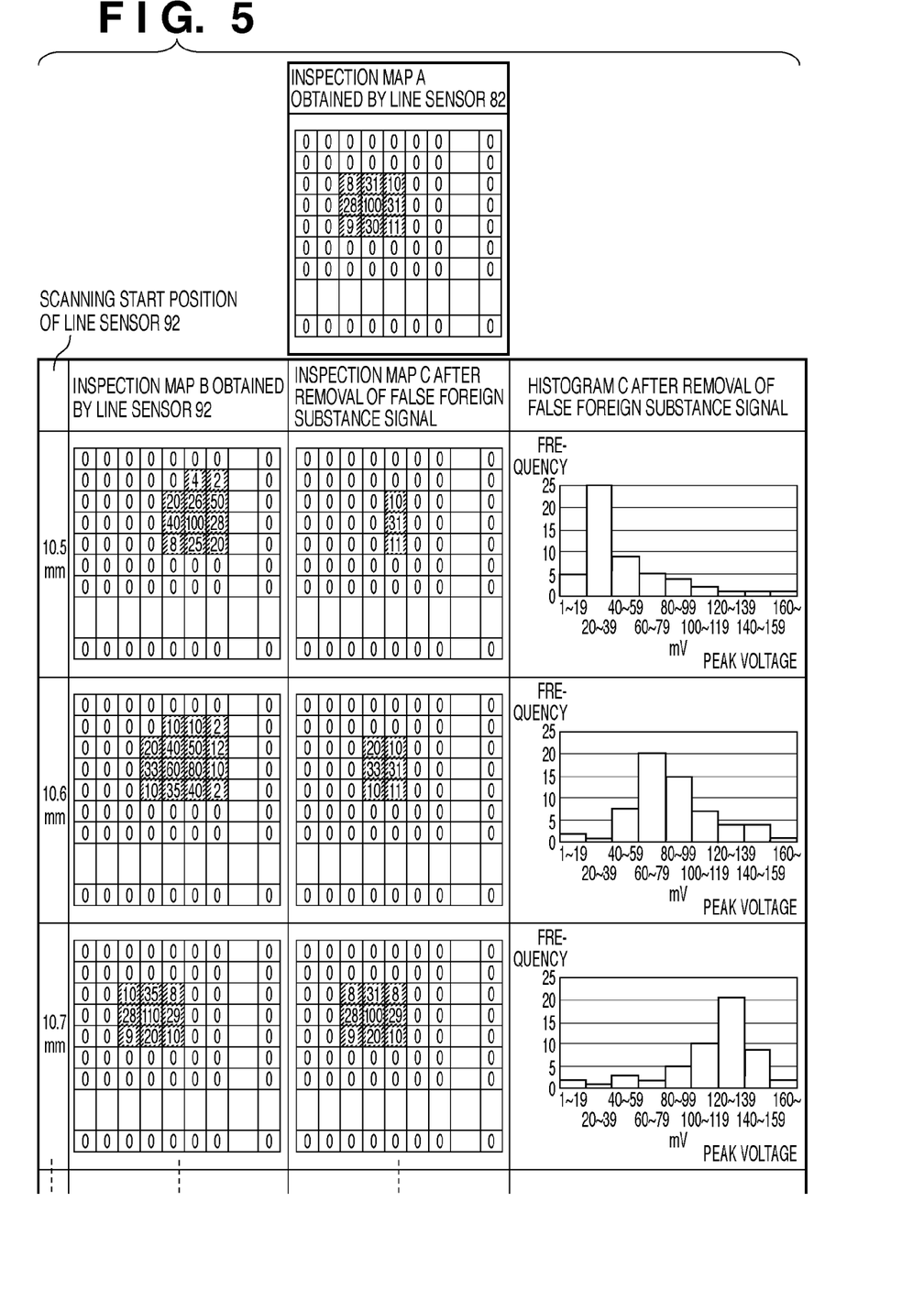
FIG. 5 is a view for explaining a technique of determining scanning start positions.

In step 104, the controller 11 performs the processing for removing a false foreign substance signal. In this step, the controller 11 calculates an inspection map C by removing false foreign substance signals from the inspection map A of the line sensor 82 stored in step 101 and the inspection map B of the line sensor 92 calculated in step 103. The inspection map C is the map obtained by extracting only the signal common to the inspection maps A and B, and is the intensity distribution of a signal, of the signals in the two inspection maps, which is located at the same position in the maps and has a lowest intensity. That is, the inspection map C indicates the overlapping degree between the intensity distributions of the signals in the inspection maps A and B of the line sensors 82 and 92.

In step 105, the controller 11 calculates a histogram D as the frequency distribution of intensities by compiling the signals in the inspection map C after removal of false foreign substance signals. Note that in this embodiment, the intensity is displayed in voltage.

In step 106, the controller 11 extracts a combination of the tentative second scanning start position (10.5 mm) tentatively set for the line sensor 92 and the intensity (peak voltage) corresponding to the maximal frequency on the histogram D, and causes the foreign substance inspection apparatus to store it.

In step 107, the controller 11 changes the positional relationship between the scanning start positions of the two line sensors by adding 0.1 mm to the tentative second scanning start position tentatively set in step 102 and setting the next tentative second scanning start position to 10.6 mm.

In the same manner, subsequently, the controller 11 causes the foreign substance inspection apparatus to perform foreign substance inspection a plurality number of times while changing the tentative second scanning start position of the line sensor 92 by 0.1 mm each time. Assume that in this case, the changing range of the tentative second scanning start position of the line sensor 92 is the range in which the tentative second scanning start position of the line sensor 92 is spaced apart from the origin switch position by 10.5 mm to 11.0 mm.

In step 108, the controller 11 checks whether the tentative second scanning start position falls within the changing range, that is, within 11.0 mm. If YES in step 108, the process returns to step 103.

Figure 6:
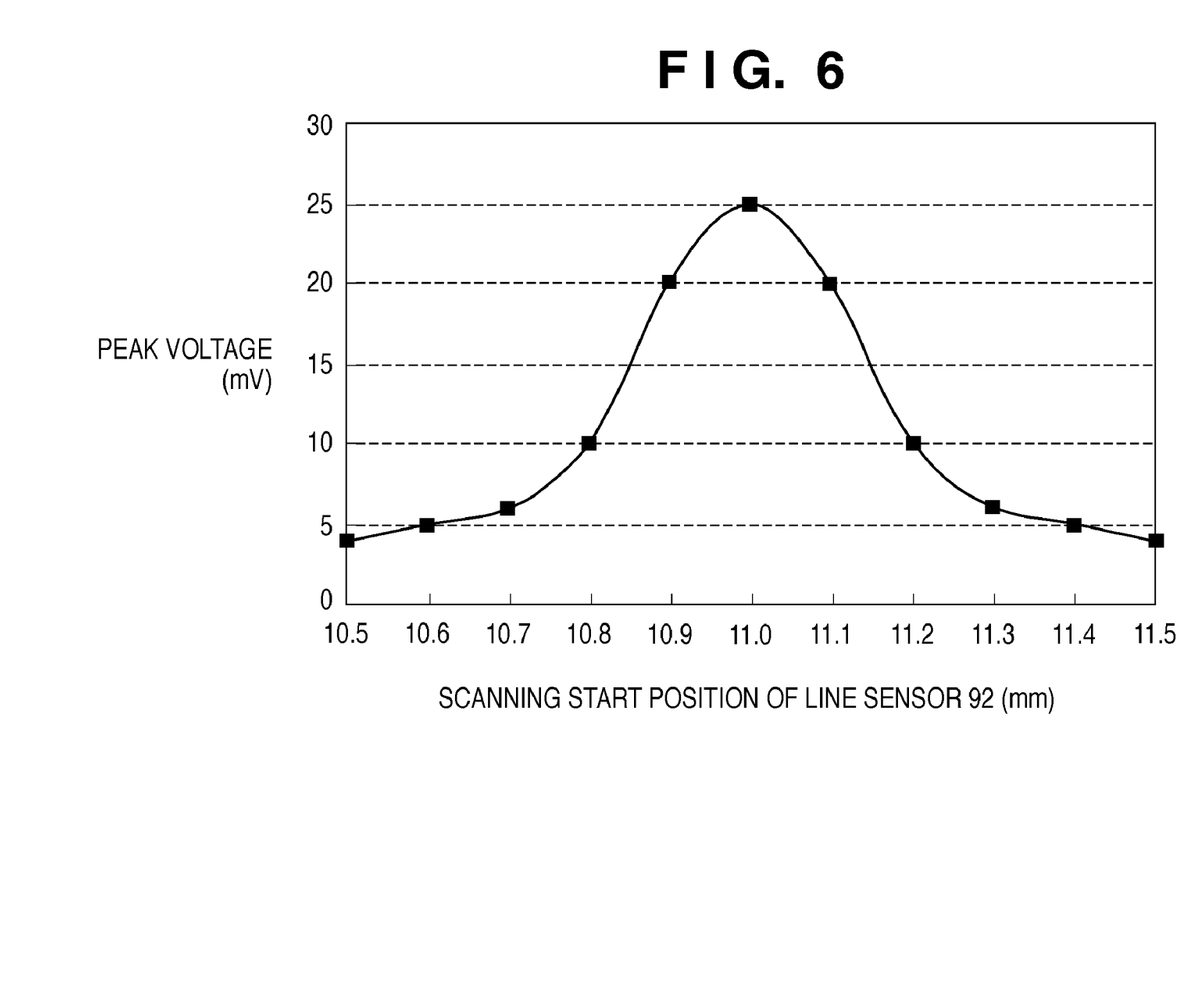
FIG. 6 is a graph showing the relationship between scanning start positions and peak voltages.

In step 109, the controller 11 determines the scanning start position of the line sensor 92 to inspect a foreign substance on the surface of the object. The controller 11 obtains the tentative second scanning start position at which the peak voltage becomes maximum from the graph shown in FIG. 6 which depicts the relationship between the tentative second scanning start position stored in step 106 and the peak voltage. The controller 11 then causes the foreign substance inspection apparatus to store the tentative second scanning start position as a correct scanning start position.

According to the above technique, the controller 11 determines the correct scanning start position of the line sensor 92 based on the signal intensity at which the intensity of common signals output from the two line sensors exhibits a maximal frequency.

Figure 8:
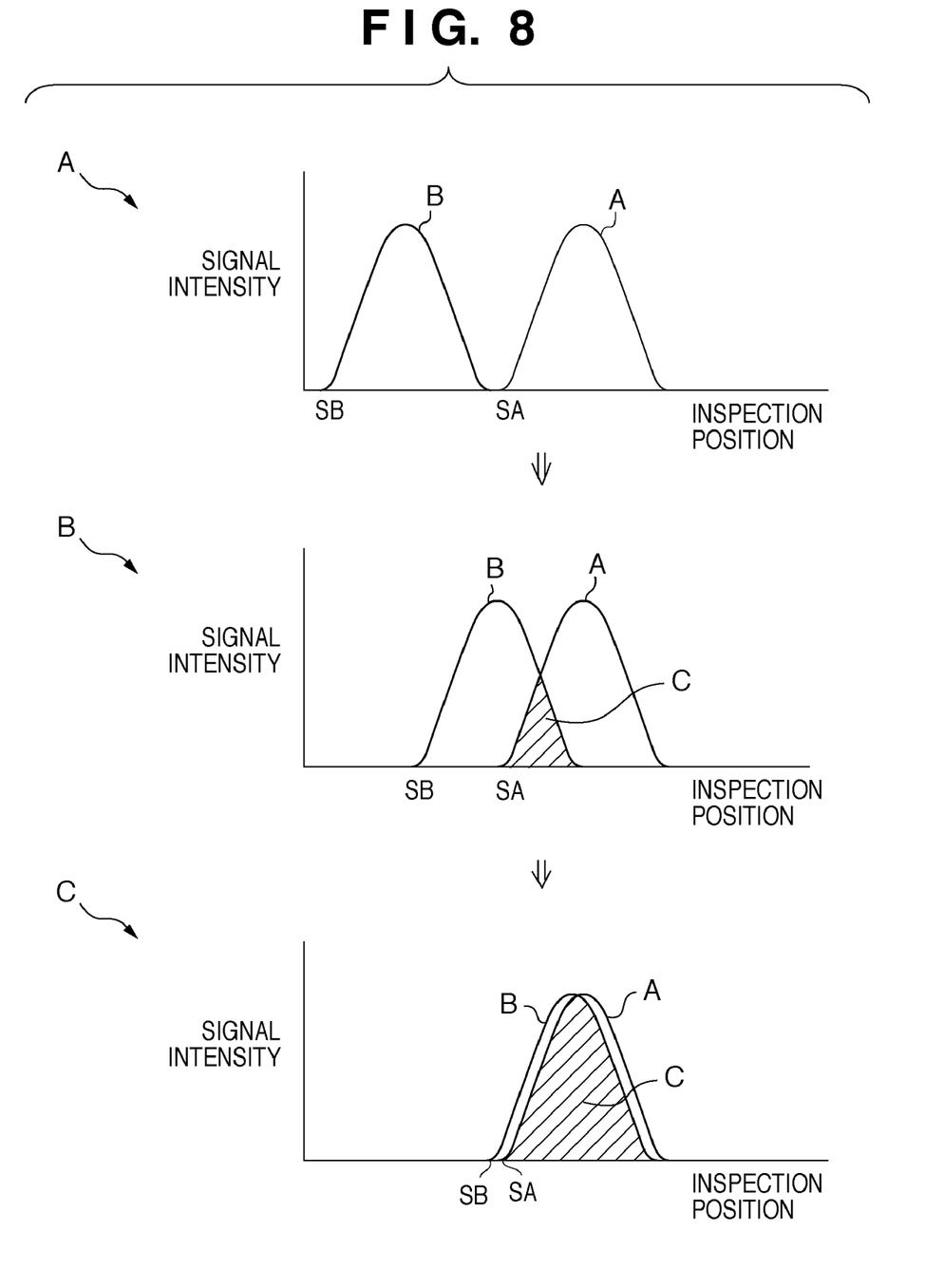
FIG. 8 is a graph for explaining a technique of determining a scanning start position.

However, the controller 11 may determine a correct scanning start position in the following manner. If the two line sensors 82 and 92 have the same sensitivity, the two line sensors 82 and 92 output signals having the same intensity distribution. If, however, tentative first and second scanning start positions SA and SB of the line sensors 82 and 92 greatly differ from each other, intensity distributions A and B of signals based on a foreign substance do not overlap each other, as denoted by reference symbol A in FIG. 8. As the tentative first and second scanning start positions of the line sensors 82 and 92 are matched, the intensity distributions A and B of the signals based on the foreign substance overlap each other (see reference symbols B and C in FIG. 8). The overlapping degree between the signal intensity distributions A and B of the signals output from the line sensors 82 and 92 has a positive correlation with the signal intensity common to the signals output from the line sensors 82 and 92 and the size of the overlapping range of the signal intensity distributions. Referring to FIG. 8 as an example, it is also possible to obtain the correct scanning start positions of the line sensors 82 and 92 based on the maximal value of the height (or the size of the base) of the overlapping portion C indicated by the hatched portion.

The correct scanning start positions of the line sensors 82 and 92 in the Y direction can also be adjusted in the same manner as in the above technique. It is therefore also possible to determine the correct scanning start positions of the line sensors 82 and 92 as positions on a two-dimensional plane.

Using the technique of the above embodiment can accurately inspect only a foreign substance without omission and without being influenced by scattered light or diffracted light from a circuit pattern or the like.

The above embodiment fixes the scanning start position of the line sensor 82 and adjusts only the scanning start position of the line sensor 92. However, it is possible to hold a known reference inspection map as data and obtain optimal scanning start positions of the line sensors 82 and 92 corresponding to the reference inspection map.

In addition, the above embodiment uses a glass plate coated with a reference particle as an object to be inspected. However, it is possible to set, as an object to be inspected, a flat object whose surface is indented or on which a pattern is drawn.

The foreign substance inspection apparatus of this embodiment can be applied to various kinds of high-precision processing apparatuses, various kinds of high-precision measurement apparatuses, and the like as well as exposure apparatuses used to manufacture semiconductor devices, liquid crystal display devices, and the like. This foreign substance inspection apparatus can effectively detect foreign substances on the inspection surfaces of objects to be processed and objects to be measured.

Figure 9:
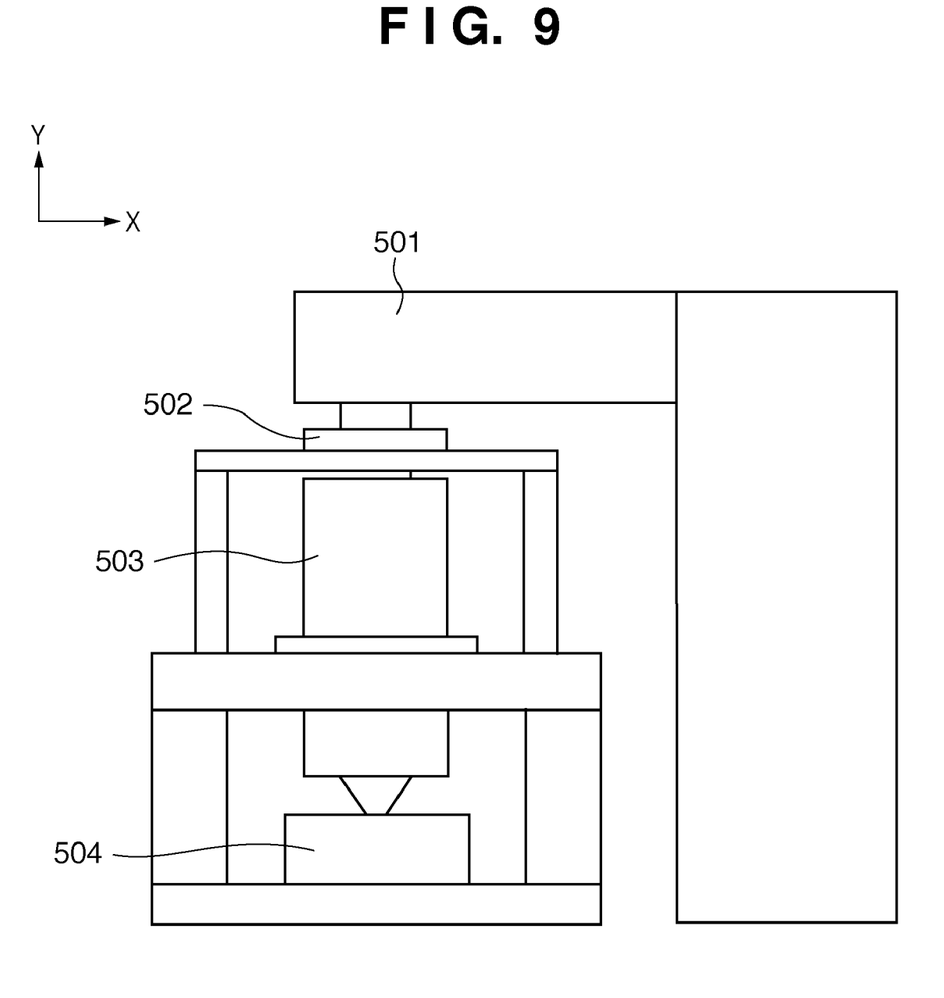
FIG. 9 is a view showing an example of an exposure apparatus.

An exemplary exposure apparatus configured to transfer a pattern of a reticle onto a substrate and expose the substrate, to which the foreign substance inspection apparatus of this embodiment is applied, will be described below. As shown in FIG. 9, the exposure apparatus includes an illumination system 501, a reticle stage 502 on which a reticle is mounted, a projection optical system 503, and a substrate stage 504 which holds a substrate. A driving mechanism (not shown) scans/moves the substrate stage 504 in the Y direction, and moves the stage step by step in the X direction, as described above. The exposure apparatus projects and scan-expose a circuit pattern formed on a reticle onto a substrate.

The illumination system 501 illuminates a reticle on which a circuit pattern is formed, and has a light source unit and illumination optical system. The light source unit uses, for example, a laser as a light source. The laser can be, for example, an ArF excimer laser with a wavelength of about 193 nm, a KrF excimer laser with a wavelength of about 248 nm, or an F2 excimer laser with a wavelength of about 153 nm. However, the type of laser is not particularly limited to an excimer laser and may be, for example, a YAG laser, and the number of lasers is not particularly limited, either. When a laser is used as the light source, an optical system for shaping a parallel beam from the laser beam source into a desired beam shape, and an optical system for converting a coherent laser beam into an incoherent one can be used. Also, the light source which can be used for the light source unit is not particularly limited to a laser, and one or a plurality of mercury lamps or xenon lamps can be used. The illumination optical system is an optical system which illuminates a mask and includes, for example, a lens, mirror, light integrator, and stop.

The projection optical system 503 can be, for example, an optical system having a plurality of lens elements alone, an optical system having a plurality of lens elements and at least one concave mirror, an optical system having a plurality of lens elements and at least one diffraction optical element such as a kinoform, or an all-mirror type optical system.

The reticle stage 502 and the substrate stage 504 can be driven by, for example, a linear motor. The respective stages synchronously move. Actuators (driving mechanisms) (not shown) are provided to the substrate stage 504 and the reticle stage 502 to align the reticle pattern on the substrate.

A method of manufacturing a device such as a semiconductor integrated circuit device or a liquid crystal display device by using the above exposure apparatus will be exemplified next.

Devices are manufactured by an exposing step of exposing a substrate using the above exposure apparatus, a developing step of developing the substrate exposed in the exposing step, and other known step (e.g., etching, resist removal, dicing, bonding, and packaging steps) of processing the substrate developed in the developing step.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-192686, filed Jul. 25, 2008, which is hereby incorporated by reference herein in its entirety.

What is claimed is:

1. An inspection apparatus comprising:
   a light projecting unit configured to project linear light on a surface of an object to be inspected;
   a first light receiving unit and a second light receiving unit configured to receive scattered light of light projected on the surface by the light projecting unit, which is generated by the surface; and
   a controller configured to relatively scan the light projecting unit, the first light receiving unit, and the second light receiving unit along the surface while maintaining a positional relationship between the light projecting unit, the first light receiving unit, and the second light receiving unit and determine the presence/absence of a foreign substance on the surface based on intensity distributions of signals output from the first light receiving unit and the second light receiving unit,
   the controller causing the inspection apparatus to perform foreign substance inspection a plurality number of times while changing a positional relationship between a tentative first start position at which the first light receiving unit starts scanning and a tentative second start position at which the second light receiving unit starts scanning,
   calculating an overlapping degree between an intensity distribution of a signal output from the first light receiving unit and an intensity distribution of a signal output from the second light receiving unit for each of the plurality of foreign substance inspections, and
   determining a scanning start position of each of the first light receiving unit and the second light receiving unit to inspect the surface of the object based on the positional relationship between the tentative first start position and the tentative second start position which exhibits a maximal overlapping degree among the plurality of calculated overlapping degrees.

2. The apparatus according to claim 1, wherein the overlapping degree is defined by an intensity distribution comprised of the lower intensity values of pairs of intensity values at positions having intensity values of higher than 0 from both the first light receiving unit and the second light receiving unit.

3. The apparatus according to claim 2, wherein the controller determines the scanning start position of each of the first light receiving unit and the second light receiving unit based on a maximal intensity value of the intensity distribution.

4. The apparatus according to claim 2, wherein the controller determines the scanning start position of each of the first light receiving unit and the second light receiving unit based on a number of the positions having intensity values of higher than 0 from both the first light receiving unit and the second light receiving unit.

5. The apparatus according to claim 2, wherein the controller calculates a frequency distribution of intensities from the intensity distribution of the signal having the minimal intensity for each of the plurality of foreign substance inspections, extracts intensities with a maximal frequency in the calculated frequency distribution, and determines the scanning start position of each of the first light receiving unit and the second light receiving unit based on the positional relationship which exhibits a maximal intensity of the plurality of extracted intensities with the maximal frequency.

6. The apparatus according to claim 1, wherein the scanning start position which the controller determines for each of the first light receiving unit and the second light receiving unit is a position on a two-dimensional plane.

7. An exposure apparatus which exposes a substrate to radiant energy via a pattern of a reticle, the apparatus comprising an inspection apparatus configured to inspect a foreign substance on a surface of the reticle,
the inspection apparatus comprising
a light projecting unit configured to project linear light on a surface of an object to be inspected,
a first light receiving unit and a second light receiving unit configured to receive scattered light, of light projected on the surface by the light projecting unit, which is generated by the surface, and
a controller configured to relatively scan the light projecting unit, the first light receiving unit, and the second light receiving unit along the surface while maintaining a positional relationship between the light projecting unit, the first light receiving unit, and the second light receiving unit and determine the presence/absence of the foreign substance on the surface based on intensity distributions of signals output from the first light receiving unit and the second light receiving unit,
the controller causing the inspection apparatus to perform foreign substance inspection a plurality number of times while changing a positional relationship between a tentative first start position at which the first light receiving unit starts scanning and a tentative second start position at which the second light receiving unit starts scanning,
calculating an overlapping degree between an intensity distribution of a signal output from the first light receiving unit and an intensity distribution of a signal output from the second light receiving unit for each of the plurality of foreign substance inspections, and
determining a scanning start position of each of the first light receiving unit and the second light receiving unit to inspect the surface of the object based on the positional relationship between the tentative first start position and the tentative second start position which exhibits a maximal overlapping degree among the plurality of calculated overlapping degrees.

8. A method of manufacturing a device, the method comprising:
exposing a substrate to radiant energy via a pattern of a reticle using an exposure apparatus;
developing the exposed substrate; and
processing the developed substrate to manufacture the device,
wherein the exposure apparatus comprises an inspection apparatus configured to inspect a foreign substance on a surface of the reticle,
the inspection apparatus comprising
a light projecting unit configured to project linear light on a surface of an object to be inspected,
a first light receiving unit and a second light receiving unit configured to receive scattered light, of light projected on the surface by the light projecting unit, which is generated by the surface, and
a controller configured to relatively scan the light projecting unit, the first light receiving unit, and the second light receiving unit along the surface while maintaining a positional relationship between the light projecting unit, the first light receiving unit, and the second light receiving unit and determine the presence/absence of the foreign substance on the surface based on intensity distributions of signals output from the first light receiving unit and the second light receiving unit,
the controller causing the inspection apparatus to perform foreign substance inspection a plurality number of times while changing a positional relationship between a tentative first start position at which the first light receiving unit starts scanning and a tentative second start position at which the second light receiving unit starts scanning,
calculating an overlapping degree between an intensity distribution of a signal output from the first light receiving unit and an intensity distribution of a signal output from the second light receiving unit for each of the plurality of foreign substance inspections, and
determining a scanning start position of each of the first light receiving unit and the second light receiving unit to inspect the surface of the object based on the positional relationship between the tentative first start position and the tentative second start position which exhibits a maximal overlapping degree among the plurality of calculated overlapping degrees.

9. An inspection apparatus comprising:
a projecting unit configured to project linear light on a surface of an object;
a first receiving unit and a second receiving unit configured to receive scattered light of projected linear light; and
a controller configured to scan the projecting unit, the first and second receiving units, along the surface while maintaining a positional relationship between the projecting unit, the first and second receiving units, and to determine the presence/absence of a foreign substance on the surface based on intensity distributions of signals output from the first and second receiving units,
wherein the controller causes the inspection apparatus to perform foreign substance inspection a plurality number of times while changing a positional relationship between a first start position at which the first receiving unit starts scanning and a second start position at which the second receiving unit starts scanning, calculates an overlapping degree between an intensity distribution of a signal output from each of the first and second receiving units for each of the plurality of foreign substance inspections, and determines a scanning start position of each of the first and second receiving units to inspect the surface of the object based on the overlapping degree.

10. The apparatus according to claim 9, wherein the controller determines a scanning start position of each of the first and second receiving units to inspect the surface of the object based on a positional relationship between the first and second start positions which exhibits a maximal overlapping degree among the plurality of calculated overlapping degrees.

11. The apparatus according to claim 10, wherein the overlapping degree is defined by an intensity distribution comprising the lower intensity values of pairs of intensity values at positions having intensity values of higher than 0 from both the first and second receiving units.

12. The apparatus according to claim 11, wherein the controller determines a scanning start position of each of the first and second receiving units based on a maximal intensity value of the intensity distribution.

13. The apparatus according to claim 11, wherein the controller determines a scanning start position of each of the first and second receiving units based on a number of the positions having intensity values of higher than 0 from both the first and second receiving units.

14. The apparatus according to claim 11, wherein the controller calculates a frequency distribution of intensities from the intensity distribution of the signal having the minimal intensity for each of the plurality of foreign substance inspections, extracts intensities with a maximal frequency in the calculated frequency distribution, and determines a scanning start position of each of the first and second receiving units based on the positional relationship which exhibits a maximal intensity of the plurality of extracted intensities with the maximal frequency.

15. The apparatus according to claim 9, wherein a scanning start position which the controller determines for each of the first and second receiving units is a position on a two-dimensional plane.

16. An exposure apparatus which exposes a substrate to radiant energy via a pattern of a reticle, the exposure apparatus comprising the inspection apparatus according to claim 9, wherein the inspection apparatus is configured to inspect a foreign substance on a surface of the reticle.

17. A method comprising:
exposing a substrate to radiant energy via a pattern of a reticle using the exposure apparatus according to claim 16;
developing the exposed substrate; and
processing the developed substrate.

* * * * *